(12) United States Patent
Nomura

(10) Patent No.: US 9,585,742 B2
(45) Date of Patent: Mar. 7, 2017

(54) STENT

(71) Applicant: OLYMPUS CORPORATION, Tokyo (JP)

(72) Inventor: Yusuke Nomura, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/981,534

(22) Filed: Dec. 28, 2015

(65) Prior Publication Data

US 2016/0128824 A1    May 12, 2016

Related U.S. Application Data

(63) Continuation of application No. PCT/JP2014/065073, filed on Jun. 6, 2014.

(Continued)

(51) Int. Cl.
*A61F 2/04* (2013.01)
*A61F 2/82* (2013.01)
(Continued)

(52) U.S. Cl.
CPC .................. *A61F 2/04* (2013.01); *A61F 2/82* (2013.01); *A61F 2/848* (2013.01); *A61F 2/94* (2013.01);
(Continued)

(58) Field of Classification Search
CPC .... A61F 2/82; A61F 2/006; A61F 2/06; A61F 2/848; A61F 2/04
(Continued)

(56) References Cited

U.S. PATENT DOCUMENTS 6,989,027 B2 * 1/2006 Allen .................... A61F 2/2412
606/200
7,993,411 B2 * 8/2011 Kennedy, II ............ A61L 27/34
604/8

(Continued)

FOREIGN PATENT DOCUMENTS

JP      S60180442 U    11/1985
JP      H067453 A      1/1994
(Continued)

OTHER PUBLICATIONS

Sep. 16, 2014 International Search Report issued in International Patent Application No. PCT/JP2014/065073.
(Continued)

*Primary Examiner* — Suzette J Gherbi
(74) *Attorney, Agent, or Firm* — Oliff PLC

(57) ABSTRACT

A stent includes a major axis member which has an internal space extending from a front end portion toward a base end portion, first opening section provided at the front end portion to communicate with the internal space, and second opening section provided at the base end portion to communicate with the internal space, and inflow prevention section which has an inflow prevention surface covering the second opening section with a gap with respect to the second opening section, wherein a first edge section of the inflow prevention surface is fixed to the major axis member closer to a base end than the second opening section, and a second edge section of the inflow prevention surface is disposed closer to a front end than the second opening section and extends from a side surface of the major axis member toward a position spaced apart therefrom outward in a radial direction.

9 Claims, 8 Drawing Sheets

Related U.S. Application Data

(60) Provisional application No. 61/845,035, filed on Jul. 11, 2013.

(51) Int. Cl.
  *A61F 2/94* (2013.01)
  *A61M 27/00* (2006.01)
  *A61F 2/848* (2013.01)

(52) U.S. Cl.
  CPC ..... *A61M 27/008* (2013.01); *A61F 2002/041* (2013.01); *A61F 2002/8486* (2013.01); *A61F 2210/0014* (2013.01); *A61F 2220/0008* (2013.01); *A61F 2220/0016* (2013.01)

(58) Field of Classification Search
  USPC .................................. 623/1.15–1.48, 23.68
  See application file for complete search history.

(56) References Cited

U.S. PATENT DOCUMENTS

| | | | | |
|---|---|---|---|---|
| 8,221,505 B2* | 7/2012 | Skerven | ............... | A61F 2/04 623/23.64 |
| 2002/0165479 A1 | 11/2002 | Wilk | | |
| 2003/0069552 A1 | 4/2003 | O'Keefe et al. | | |
| 2004/0199262 A1* | 10/2004 | Dua | ............... | A61F 2/04 623/23.7 |
| 2005/0149166 A1 | 7/2005 | Schaeffer et al. | | |
| 2005/0240280 A1 | 10/2005 | Aliski et al. | | |
| 2008/0208314 A1* | 8/2008 | Skerven | ............... | A61F 2/04 623/1.15 |
| 2009/0157184 A1* | 6/2009 | Cauthen, III | ...... | A61B 17/0057 623/17.11 |
| 2010/0114325 A1 | 5/2010 | Yang et al. | | |
| 2010/0331949 A1* | 12/2010 | Habib | ............... | A61B 18/1477 623/1.11 |
| 2012/0316632 A1* | 12/2012 | Gao | ............... | A61F 2/86 623/1.2 |
| 2013/0173016 A1* | 7/2013 | Devereux | ............... | A61F 2/88 623/23.66 |
| 2015/0182359 A1* | 7/2015 | Gerberding | ............ | A61F 2/915 623/1.11 |

FOREIGN PATENT DOCUMENTS

| | | |
|---|---|---|
| JP | 2005312897 A | 11/2005 |
| WO | 03/030981 A1 | 4/2003 |

OTHER PUBLICATIONS

Sep. 5, 2016 Office Action issued in Chinese Patent Application No. 20140038827.X.
Sep. 5, 2016 Office Action issued in Chinese Patent Application No. 201480038827.X.
Dec. 9, 2016 Extended European Search Report issued in European Application No. 14823751.4.

\* cited by examiner

STENT

This application is a continuation application based on PCT/JP2014/065073, filed on Jun. 6, 2014, claiming priority based on U.S. Provisional Patent Application No. 61/845,035, filed Jul. 11, 2013. The contents of both the US Provisional Patent Application and the PCT Application are incorporated herein by reference.

BACKGROUND OF THE INVENTION

Field of the Invention

The present invention relates to a stent implanted and used in the bile duct or the pancreatic duct.

Description of the Related Art

In the related art, with respect to a narrow portion formed in the bile duct or the pancreatic duct, implantation of the stent is performed in order to expand the narrow portion and to maintain a patency state.

For example, a stent disclosed in Japanese Unexamined Patent Application, First Publication No. H06-7453 is known. The stent is formed of polyethylene having radiolucency. The stent has a front end and a front end excretion hole, and has a base end blade section and a base end excretion hole (a second opening section) in the vicinity of a base end of the stent. When the stent is disposed in the bile duct, as a front end of a base end blade section is hooked by the duodenal papilla, the base end portion of the stent protrudes from the duodenal papilla into the lumen of the duodenum to be implanted therein. As the stent is implanted into the bile duct, excretion of the bile from the bile duct to the small intestine through the common bile pipe (an internal space) and the duodenal papilla is promoted.

SUMMARY OF THE INVENTION

A stent according to a first aspect of the present invention includes a major axis member which has an internal space extending from a front end portion toward a base end portion, a first opening section provided at the front end portion to communicate with the internal space, and a second opening section provided at the base end portion to communicate with the internal space, and an inflow prevention section which has an inflow prevention surface covering the second opening section with a gap with respect to the second opening section, wherein a first edge section of the inflow prevention surface is fixed to the major axis member closer to a base end than the second opening section, and a second edge section of the inflow prevention surface is disposed closer to a front end than the second opening section and extends from a side surface of the major axis member toward a position spaced apart therefrom outward in a radial direction.

According to a second aspect of the present invention, in the stent according to the first aspect, the second opening section may be formed in the side surface of the major axis member.

According to a third aspect of the present invention, in the stent according to the first or second aspect, the inflow prevention section may have a plurality of bony portions which is arranged in a circumferential direction of the major axis member, each having a first end section formed of a material having elasticity and fixed closer to the base end than the second opening section, and a second end section extending toward the front end in a natural state and spaced apart from a circumferential surface of the major axis member outward in the radial direction, and membranous portions which has more flexibly than the bony portions and which is formed between the bony portions at least one set of the bony portions neighboring in the circumferential direction from the first end sections to the second end sections, and which covers the second opening section.

According to a fourth aspect of the present invention, in the stent according to the third aspect, the membranous portions may be provided between the bony portions neighboring in the circumferential direction of the major axis member in an entire circumference of the major axis member, and a cutout which extends from the front end to the base end and which penetrates through the membranous portion in a thickness direction may be formed in one of the membranous portions.

According to a fifth aspect of the present invention, in the stent according to the first or second aspect, the inflow prevention section may be formed throughout an entire circumference of the major axis member.

According to a sixth aspect of the present invention, in the stent according to the first aspect, the stent may include an umbrella section in which the inflow prevention surface directed from an umbrella base end portion disposed at a base end of the stent toward the front end of the major axis member and extending from a circumferential surface of the major axis member to be spaced outward in the radial direction is formed at an entire circumference of the major axis member, a bottom section may be provided at the umbrella base end portion, the major axis member may have the second opening section between the bottom section and the base end portion of the major axis member, and the second opening section may include a crevice between the second opening section and the inflow prevention surface and is covered by the inflow prevention surface.

According to a seventh aspect of the present invention, in the stent according to the sixth aspect, the stent may include a joint member which is installed between the base end portion of the major axis member formed in a tubular shape and the umbrella base end portion, which extends from a wall section of the base end portion of the major axis member toward the umbrella base end, which is formed in a rod shape, and which connects the base end portion of the major axis member and the umbrella base end portion. The second opening section may be formed by the joint member and the major axis member.

According to an eighth aspect of the present invention, in the stent according to the first or second aspect, a valve unit, which is formed of a material having elasticity and which has a slit closed in a natural state and elastically deformed to communicate with the internal space, may be installed at the base end portion of the major axis member.

According to a ninth aspect of the present invention, in the stent according to the first or second aspect, a sealing member, which is formed of a material having elasticity and which partitions the internal space and the outside of the major axis member may be formed at the base end portion of the major axis member.

DETAILED DESCRIPTION OF THE INVENTION

First Embodiment

Hereinafter, a first embodiment of a stent 1 according to the present invention will be described with reference to FIGS. 1 to 12.

Further, in all of the following drawings, for easy understanding of the drawings, ratios of thicknesses or dimensions of components may be appropriately different from each other.

Figure 1:
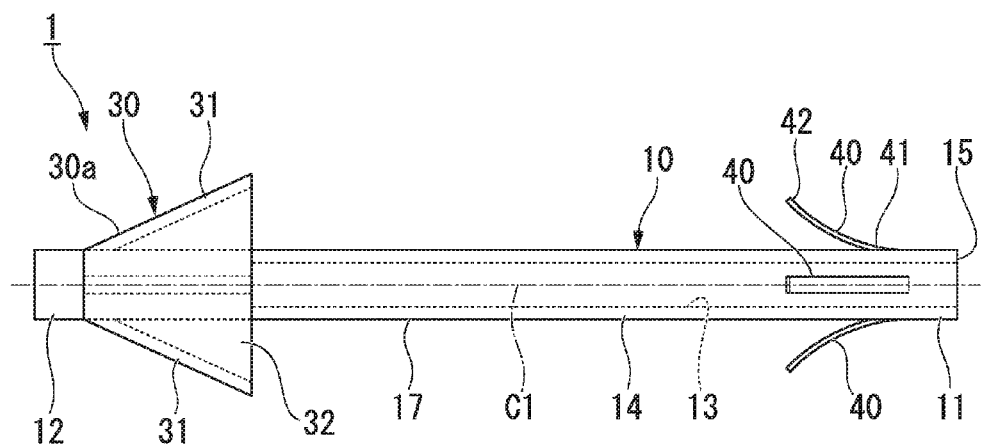
FIG. 1 is a side view of a stent according to a first embodiment of the present invention.
Figure 2:
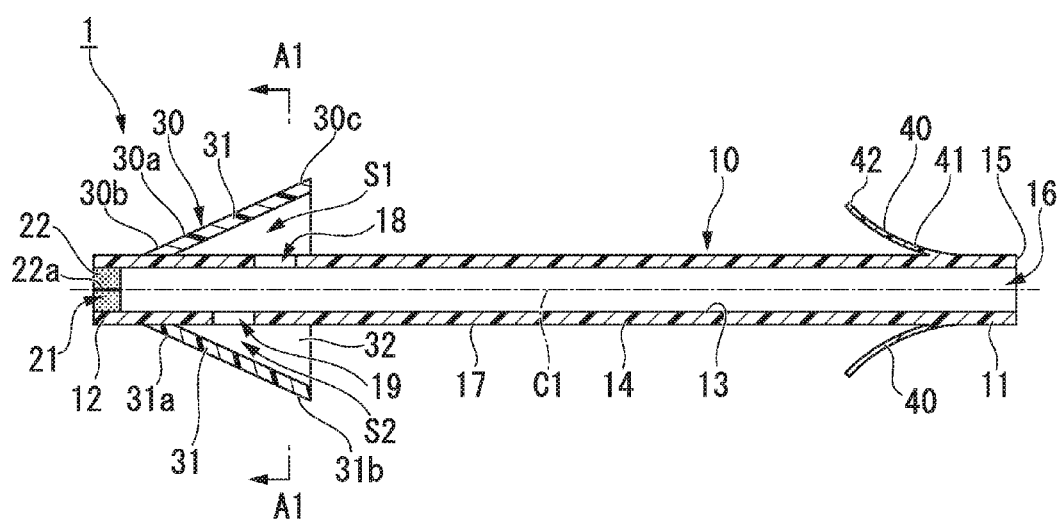
FIG. 2 is a side cross-sectional view of the stent according to the first embodiment of the present invention.

As shown in FIGS. 1 and 2, the stent 1 of the embodiment includes a main body (a major axis member) 10 and an umbrella section (an inflow prevention section) 30. An internal space 13, a first opening section 16, and second opening sections 18 and 19 are formed in the main body 10. The internal space 13 extends from a front end portion 11 toward a base end portion 12 of the main body 10. The first opening section 16 is formed in the front end portion 11 of the main body 10. The second opening sections 18 and 19 are formed in an outer circumferential surface (a side surface) 17 of the base end portion 12 of the main body 10. The umbrella section 30 has an inflow prevention surface 30a configured to entirely cover the second opening sections 18 and 19.

The main body 10 is formed of a resin material having elasticity, flexibility and biocompatibility such as urethane, polyethylene, or the like, in a tubular shape. The first opening section 16 is installed at a front end surface 15 of the main body 10. The first opening section 16 comes in communication with a portion of a front end side of the internal space 13. The second opening sections 18 and 19 are formed in a longitudinal axis (a central axis) C1 direction of the main body 10. The second opening section 18 is formed closer to the front end than the second opening section 19, and disposed at a position opposite to the second opening section 19 with the longitudinal axis (the central axis) C1 of the main body 10 therebetween. The second opening sections 18 and 19 come in communication with a portion of the base end side of the internal space 13.

A conduit line of the main body 10 is constituted by the above-mentioned internal space 13, the first opening section 16, and an opening 21 formed in a base end surface 12a of the main body 10.

Figure 3:
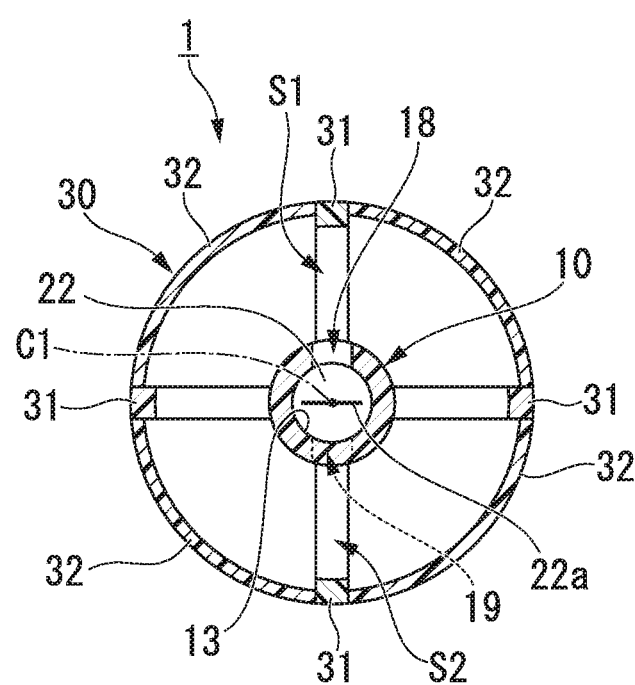
FIG. 3 is a cross-sectional view taken along line A1-A1 of FIG. 2.

A valve unit 22 formed in a columnar shape is disposed at the opening 21 of the main body 10. The valve unit 22 is formed of a material having elasticity such as rubber or the like. As shown in FIGS. 2 and 3, a slit 22a passing through the valve unit 22 in a direction (a thickness direction) along the longitudinal axis C1 is formed in the valve unit 22. While not shown, an outer circumferential surface of the valve unit 22 and an inner circumferential surface of the opening 21 are sealed by a known adhesive agent or the like having biocompatibility.

The slit 22a is closed by an elastic force of the material that forms the valve unit 22 in a natural state in which an external force except for gravity is not applied. Meanwhile, as the slit 22a is elastically deformed against the elastic force, the slit 22a can be opened. Here, an open space of the slit 22a is in communication with the internal space 13.

The slit 22a in the natural state is closed to prevent introduction of food residue into the internal space 13 through the slit 22a as described below.

As shown in FIGS. 1 and 2, the inflow prevention surface 30a of the umbrella section 30 is an outer surface of the umbrella section 30. The inflow prevention surface 30a has a first edge section 30b fixed to the outer circumferential surface 17 of the main body 10 closer to the base end side than the second opening sections 18 and 19. A second edge section 30c of the inflow prevention surface 30a is disposed at a position closer to the front end side than the second opening sections 18 and 19 and extends from the outer circumferential surface 17 of the main body 10 toward a position spaced apart outward in a radial direction.

As shown in FIGS. 2 and 3, the umbrella section 30 is formed throughout the entire circumference of the main body 10. The umbrella section 30 has a bony portion 31 and a membranous portion 32. The bony portion 31 is formed of a material having elasticity.

The bony portion 31 may be formed of a resin material having elasticity and biocompatibility such as urethane, polyethylene, or the like. Four bony portions 31 having first end sections 31a fixed closer to the base end side than the second opening sections 18 and 19 are formed in a circumferential direction of the main body 10. The membranous portion 32 extends toward the front end side while closing between the bony portions 31 neighboring in the circumferential direction.

The bony portions 31 are formed to be spaced apart outward in a radial direction from the outer circumferential surface 17 of the main body 10, while second end sections 31b extend toward the front end side in a natural state. The four bony portions 31 are spaced apart from each other in the circumferential direction and disposed at equal angles around the longitudinal axis C1 of the main body 10.

A fluorine-based resin material having a smooth surface and biocompatibility such as polytetrafluoroethylene (PTFE), perfluoroalkoxyalkane (PFA), or the like, may be appropriately used in the membranous portion 32. The membranous portion 32 is formed to be more flexible (to have lower stiffness) than the bony portion 31.

The inflow prevention surface 30a is constituted by outer surfaces of the bony portions 31 and outer surfaces of the membranous portions 32. The umbrella section 30 is opened in an umbrella shape in a natural state.

The inflow prevention surface 30a of the umbrella section 30 is formed to cover the entire second opening section 18 while being spaced by a gap S1 from the second opening section 18 outward in the radial direction of the main body 10. The gap S1 is also provided between the second opening section 18 and an inner surface 30d of the umbrella section 30 disposed at the second opening section 18 side.

The inflow prevention surface 30a is formed to cover the entire second opening section 19 while being spaced by a gap S2 from the second opening section 19 outward in the radial direction. The gap S2 is also formed between the inner surface 30d of the umbrella section 30 and the second opening section 19.

The gaps S1 and S2 are sealed by the first edge section 30b of the inflow prevention surface 30a and the main body 10 at the base end side.

In the embodiment, as shown in FIGS. 1 and 2, four flaps 40 (one of the flaps 40 is not shown) are fixed to the front end portion 11 of the main body 10.

The flap 40 includes a first flap end section 41 and a second flap end section 42. The first flap end section 41 is fixed to the front end portion 11 of the main body 10. The second flap end section 42 extends toward a central section 14 of the main body 10 along the longitudinal axis C1, and is formed to be gradually spaced apart from the outer circumferential surface 17 of the main body 10 outward in the radial direction. The flap 40 is formed of the same material as the main body 10, and the first end section 41 thereof is fixed to the main body 10 by thermal welding, adhesion, or the like.

Next, an implantation method of the stent 1 according to the present invention for implanting the stent 1 having the above-mentioned configuration into the bile duct of a patient will be described below.

Figure 4:
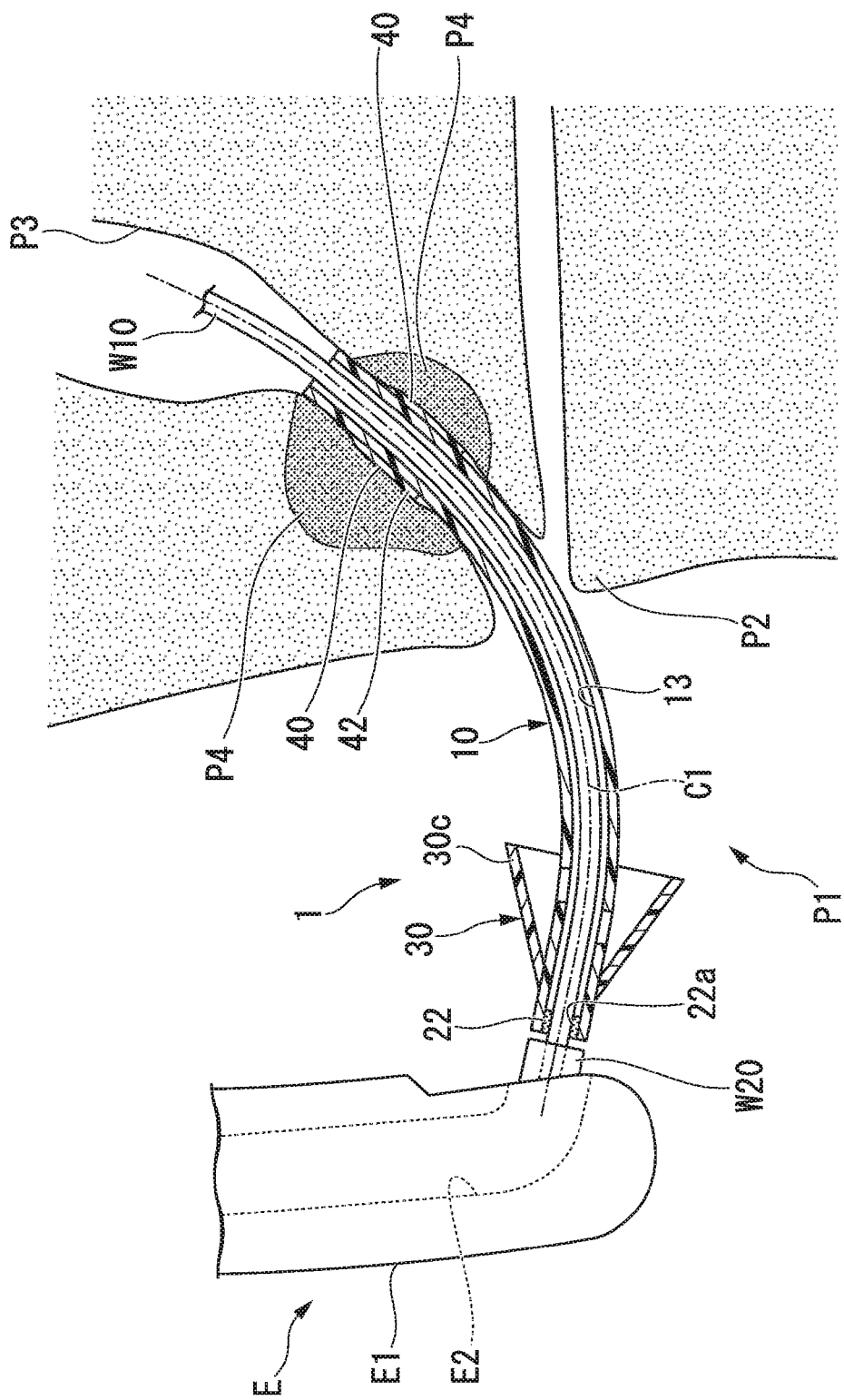
FIG. 4 is a view for describing a sequence of implanting the stent according to the first embodiment of the present invention.

First, a user such as an operator inserts a lateral vision type endoscope into a body of a patient from a natural opening such as a mouth or the like, and as shown in FIG. 4, a front end of an insertion section E1 of an endoscope E is inserted into a duodenum P1 to advance to the vicinity of a duodenal papilla P2.

Next, a user inserts a guide catheter (a rod-shaped member) W10 into a channel E2 of the endoscope E from a forceps port (not shown) of the endoscope E. An outer diameter of the guide catheter W10 is selected to be slightly smaller than an inner diameter of the main body 10 of the stent 1.

A front end of the guide catheter W10 protrudes from a front end opening of the channel E2 toward the duodenal papilla P2 while appropriately manipulating a sitting-up table (not shown) of the endoscope E. Then, the front end of the guide catheter W10 is inserted into a bile duct P3 from the duodenal papilla P2.

The user checks a shape of a narrow portion P4 between the duodenal papilla P2 and the bile duct P3 through X-ray illumination, and selects the stent 1 having a length such that a length from the second edge section 30c of the umbrella section 30 when opened to the second end section 42 of the flap 40 is substantially equal to a distance from the duodenal papilla P2 to passing the narrow portion P4 of the bile duct P3.

In the outside of the body of the patient, the valve unit 22 is elastically deformed such that the slit 22a of the valve unit 22 of the stent 1 is opened. A base end side of the guide catheter W10 is inserted through the internal space 13 and the deformed slit 22a.

A pusher catheter (a tubular member) W20 is fitted onto a portion of the guide catheter W10 disposed closer to the base end side than the main body 10. The pusher catheter W20 is selected to have an outer diameter and an inner diameter that are substantially equal to an outer diameter and an inner diameter of the main body 10.

Figure 5:
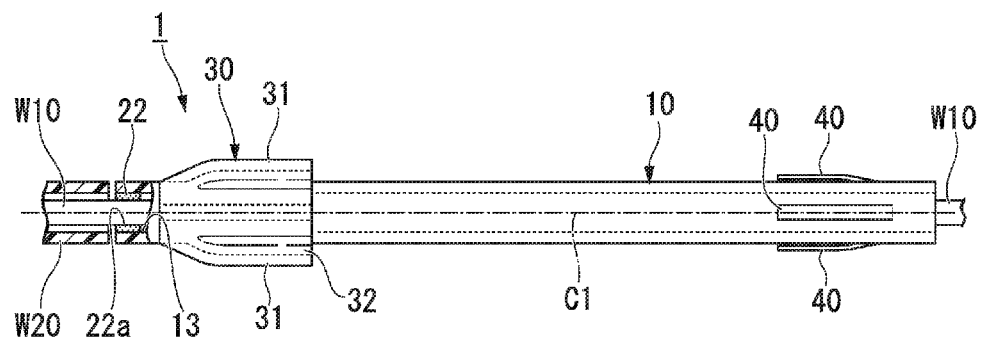
FIG. 5 is a side view of the stent according to the first embodiment of the present invention deformed to be introduced into the body, a portion of which is cutaway.

As shown in FIG. 5, the umbrella section 30 is pressed against the elastic force of the bony portion 31 toward the longitudinal axis C1 throughout the entire circumference, and the bony portion 31 or the membranous portion 32 are deformed at the longitudinal axis C1 side. Here, the membranous portion 32 is folded in the circumferential direction, and the umbrella section 30 is closed.

The pusher catheter W20 is moved toward (pushed into) the front end side with respect to the guide catheter W10 and the stent 1 is inserted into the channel E2 of the endoscope E from the forceps port. As a result, the flaps 40 pushed against the inner circumferential surface of the channel E2 are deformed toward the longitudinal axis C1 to be closed. That is, the flaps 40 opened outside in the radial direction and the umbrella section 30 opened in an umbrella shape in a natural state are introduced into the channel E2 in a state in which they are closed with small outer diameters.

If the flaps 40 protrude from the front end opening of the channel E2 when the pusher catheter W20 is pushed, the flaps 40 are opened outward in the radial direction by the elastic force thereof. When the flaps 40 of the stent 1 are inserted into the narrow portion P4 of the bile duct P3 through the channel E2, the flaps 40 are pushed against the inner circumferential surface of the narrow portion P4 are deformed toward the longitudinal axis C1.

As shown in FIG. 4, when the umbrella section 30 protrudes from the front end opening of the channel E2, the umbrella section 30 is opened in an umbrella shape by the elastic force thereof.

Figure 6:
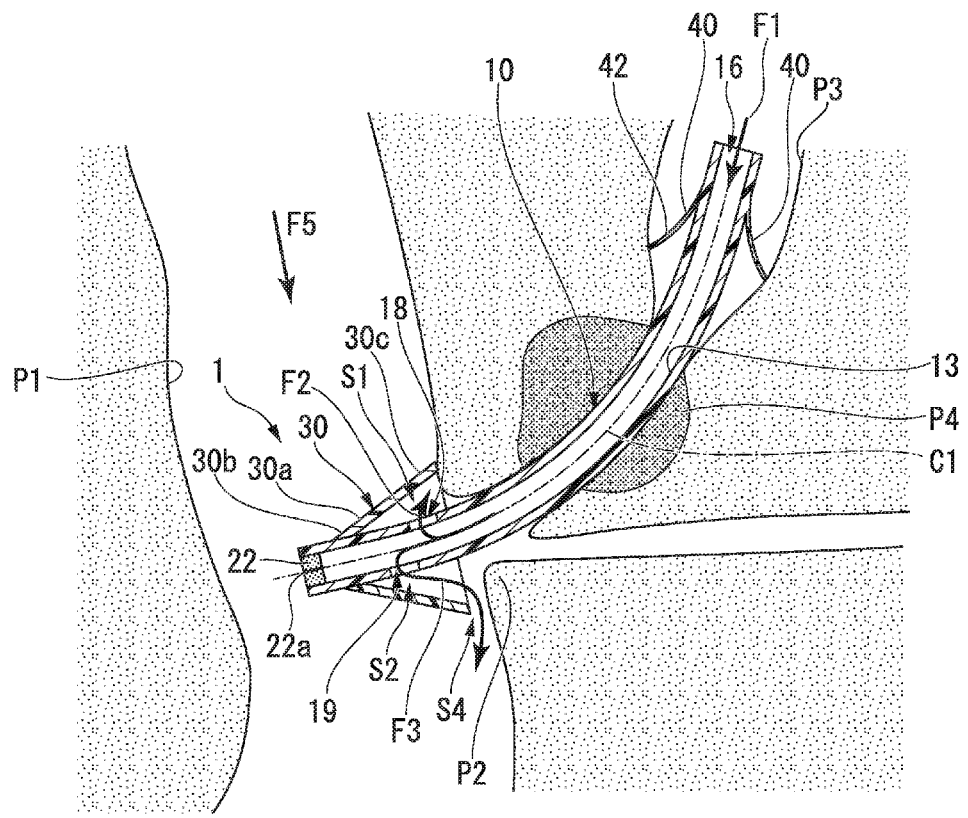
FIG. 6 is a view for describing a sequence of implanting the stent according to the first embodiment of the present invention.

As shown in FIG. 6, when the stent 1 is further inserted into the bile duct P3 and the flaps 40 pass the narrow portion P4, the flaps 40 are opened and the flaps 40 are hooked at the front end side of the narrow portion P4.

Here, since the stent 1 in which the length from the second edge section 30c of the umbrella section 30 to the second end section 42 of the flap 40 is set as described above is selected, the second edge section 30c of the umbrella section 30 is also hooked at the duodenal papilla P2. Accordingly, the umbrella section 30 protrudes from the duodenal papilla P2 into a lumen of the duodenum P1.

The guide catheter W10 is moved (returned) toward the base end with respect to the pusher catheter W20 to draw the guide catheter W10 from the main body 10 while holding the position of the pusher catheter W20. The valve unit 22 is elastically deformed and the slit 22a is closed.

The second edge section 30c of the umbrella section 30 comes in contact with the duodenal papilla P2 at a portion thereof around the longitudinal axis C1, and does not come in contact with the entire circumference. Accordingly, a crevice S4 is formed between a portion in the circumferential direction of the second edge section 30c of the umbrella section 30 and the duodenal papilla P2. That is, the stent 1 is implanted into the bile duct P3 in a state in which the crevice S4 is formed such that food residue is not introduced between the portion in the circumferential direction of the second edge section 30c of the umbrella section 30 and the duodenal papilla P2.

The guide catheter W10 and the pusher catheter W20 are drawn to the outside through the channel E2 of the endoscope E to draw the insertion section E1 of the endoscope E from the mouth of the patient.

Bile supplied into the bile duct P3 with respect to the stent 1 implanted into the bile duct P3 enters the internal space 13 from the first opening section 16 as shown by an arrow F1. The bile flowing to the outside of the main body 10 from the second opening sections 18 and 19 as shown by arrows F2 and F3 collides with the umbrella section 30 spaced apart by the gaps S1 and S2 from the second opening sections 18 and 19 outward in the radial direction of the main body 10. Since the second opening sections 18 and 19 closer to the base end side than the gaps S1 and S2 are closed by the main body 10 and the umbrella section 30, the bile flowing to the outside of the main body 10 from the second opening sections 18 and 19 flows toward the front end, and the bile goes to the outside of the umbrella section 30 from the crevice S4 between the umbrella section 30 and the duodenal papilla P2 to pass the duodenum P1 toward downstream (to the small intestine).

In this way, the bile flowing to the outside from the second opening sections 18 and 19 does not simply flow to the outside in the radial direction but flows outward in the radial direction through the crevice S4 after the bile is blocked by the umbrella section 30 and flows toward the front end once. That is, the bile flowing to the outside of the main body 10 from the second opening sections 18 and 19 flows in an S shape as a whole when seen in a side view to arrive at the outside of the umbrella section 30.

Further, food residue arriving at the duodenum P1 from the stomach (not shown) as shown by an arrow F5 abuts the inflow prevention surface 30a of the umbrella section 30 protruding in the lumen of the duodenum P1. However, since the inflow prevention surface 30a of the umbrella section 30 covers the second opening sections 18 and 19, it is prevented that the food residue is introduced into the internal space 13 of the main body 10 from the second opening sections 18 and 19.

Since the umbrella section 30 is formed throughout the entire circumference of the main body 10, regardless of an orientation in the circumferential direction of the stent 1 implanted into the bile duct P3, it is prevented that the food residue flowing as shown by the arrow F5 is introduced into the internal space 13 of the main body 10 from the second opening sections 18 and 19.

According to the stent 1 of the embodiment, the second opening sections 18 and 19 are formed in the outer circumferential surface 17 of the base end portion 12 of the main body 10, and the inflow prevention surface 30a of the umbrella section 30 is formed to be spaced apart by the gaps S1 and S2 from the second opening sections 18 and 19 outward in the radial direction of the main body 10. For this reason, the food residue flowing through the duodenum P1 varies a direction of a flow abutting the inflow prevention surface 30a and flows from the duodenum P1 toward the small intestine. Accordingly, since the food residue flows from the second opening sections 18 and 19, it is possible to prevent from flowing backward to the bile duct P3 through the internal space 13 of the main body 10. Meanwhile, the bile flowing into the internal space 13 from the first opening section 16 can flow out of the second opening sections 18 and 19, and then, can flow in an S shape when seen in a side view to flow to the outside of the umbrella section 30 through the crevice S4.

As the second opening sections 18 and 19 are formed in the base end portion 12 of the main body 10, the bile can be easily discharged to the outside at the same degree as the stent of the related art formed in a tubular shape.

The umbrella section 30 has the bony portion 31 and the membranous portion 32. When a holding force of deforming the bony portion 31 toward the longitudinal axis C1 is removed, the umbrella section 30 is opened outside in the radial direction by the elastic force of the bony portion 31, and the umbrella section 30 can be hooked by the duodenal papilla P2. Since the umbrella section 30 is introduced into the body of the patient in a state in which the umbrella section 30 is closed with a small outer diameter, a burden applied to the patient upon insertion of the stent 1 can be reduced.

As the membranous portion 32 formed more flexibly than the bony portion 31 is provided between the bony portions 31 neighboring in the circumferential direction, the entire umbrella section 30 can be flexibly formed while maintaining the elastic force for opening as an umbrella shape in a natural state. Since the umbrella section 30 has the bony portions 31, an open shape of the umbrella section 30 in the natural state can be easily held.

Since the umbrella section 30 is formed throughout the entire circumference of the main body 10, regardless of an orientation in the circumferential direction of the stent 1 implanted into the bile duct P3, it is possible to prevent that the food residue is introduced into the internal space 13 of the main body 10 from the second opening sections 18 and 19.

The valve unit 22 having the slit 22a is installed at the base end portion 12 of the main body 10. Since the slit 22a in the natural state is closed, it is possible to prevent that the food residue is introduced into the internal space 13 from the outside through the slit 22a.

As the guide catheter W10 is inserted into the slit 22a that is elastically deformed, the stent 1 of the embodiment can be implanted into the bile duct P3 using the general guide catheter W10 and pusher catheter W20 used in the implantation of the stent of the related art.

In addition, according to the implantation method of the stent 1 according to the embodiment, the stent 1 configured to prevent a backward flow of the food residue can be implanted into the bile duct P3 using the guide catheter W10 and the pusher catheter W20 of the related art.

The configuration of the stent 1 according to the embodiment may be variously modified as described below.

Figure 7:
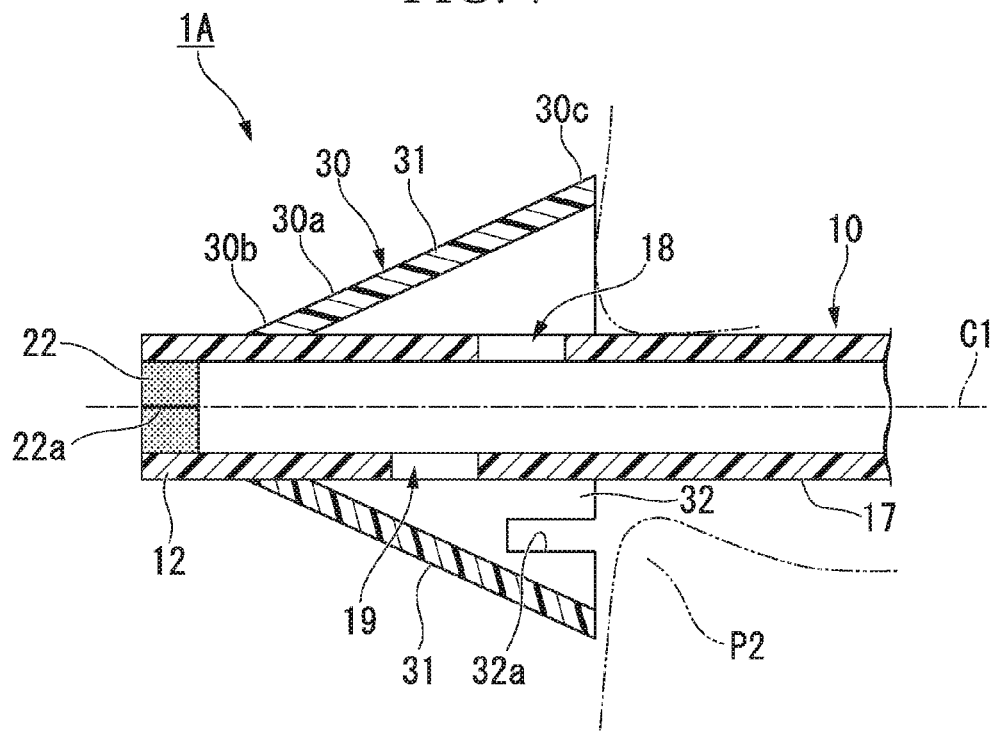
FIG. 7 is a cross-sectional view of a base end portion of a stent according to a variation of the first embodiment of the present invention.

A variation of the stent according to the embodiment is shown in FIG. 7. In the variation, the umbrella section 30 having a plurality of bony portions 31 and membranous portions 32 formed between the neighboring bony portions 31 is formed such that the entire circumference of the major axis member 10 is covered by the membranous portions 32 and the bony portions 31. For example, like a stent 1A shown in FIG. 7, in the umbrella section 30, a cutout 32a extending from a front end toward a base end may be formed at one of the membranous portions 32. The cutout 32a passes through the membranous portion 32 in a thickness direction of the membranous portion 32. The stent 1A is disposed such that the cutout 32a is positioned at a downstream (the small intestine) side when the second edge section 30c of the umbrella section 30 is hooked by the duodenal papilla P2.

As the cutout 32a is formed at the membranous portion 32 at a portion of the umbrella section 30, when the second edge section 30c of the umbrella section 30 is hooked by the duodenal papilla P2, the bile is discharged to the outside of the umbrella section 30 through the cutout 32a. Accordingly, the bile can be more securely discharged to the outside of the umbrella section 30.

Figure 8:
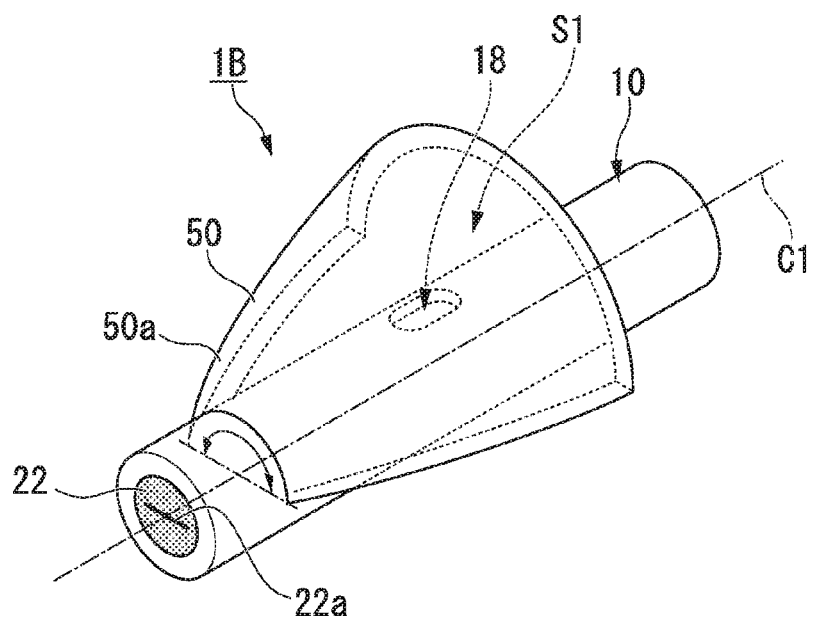
FIG. 8 is a perspective view of the base end portion of the stent according to the variation of the first embodiment of the present invention.
Figure 9:
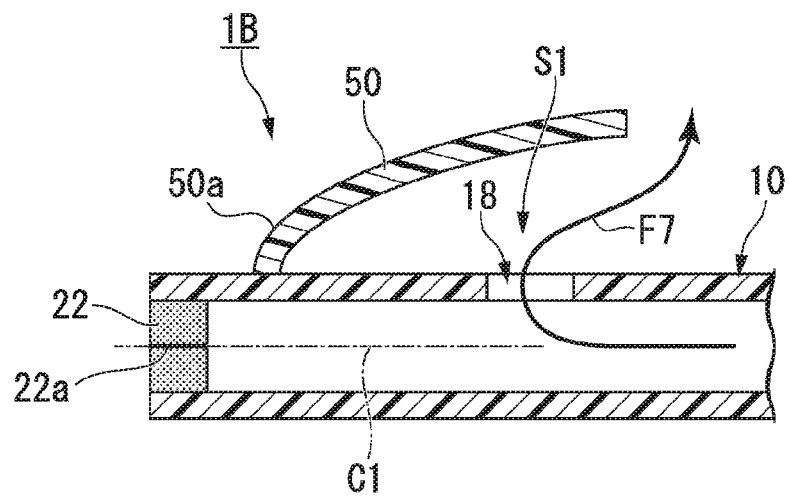
FIG. 9 is a side cross-sectional view of the base end portion of the stent of FIG. 8.

Another variation of the stent according to the embodiment is shown in FIGS. 8 and 9. Like a stent 1B shown in FIGS. 8 and 9, an umbrella section 50 may be formed at substantially half of the circumference of the main body 10. The umbrella section 50 is not constituted by the bony portions 31 and the membranous portions 32 having different stiffness like the umbrella section 30 of the embodiment. The umbrella section 50 is configured by forming a sheet shape thicker than the above-mentioned membranous portion 32, using a fluorine-based resin material. While the umbrella section 50 is opened outward in the radial direction by the elastic force thereof in a natural state, the outer diameter can be deformed to be smaller when pushed toward the longitudinal axis C1 from the outside in a radial direction. The outer surface of the umbrella section 50 constitutes an inflow prevention surface 50a.

While the second opening sections 18 and 19 are formed at the main body 10 in the embodiment, only one second opening section 18 is formed at the main body 10 in the variation. The gap S1 between the second opening section 18 and the umbrella section 50 comes in communication with the outside of the main body 10 in the circumferential direction of the main body 10.

When the stent 1B having the above-mentioned configuration is implanted into the bile duct P3, the umbrella section 50 may be implanted to be disposed at an upstream (the stomach) side.

The food residue flowing from the stomach (not shown) abuts the inflow prevention surface 50a of the umbrella section 50 to be directed toward a downstream side. As shown by an arrow F7 of FIG. 9, bile discharged to the outside of the main body 10 from the second opening section 18 abuts the umbrella section 50 to be directed toward the front end, and thus, flows in an S shape when seen in a side view.

Figure 10:
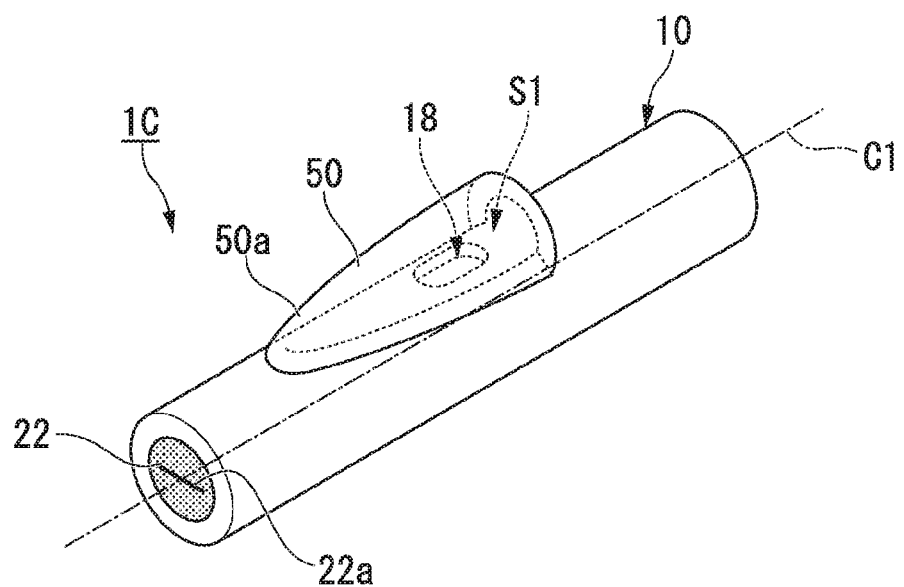
FIG. 10 is a perspective view of the base end portion of the stent according to the variation of the first embodiment of the present invention.

In addition, in addition to the stent 1B of the variation shown in FIGS. 8 and 9, a stent 1C of a variation may be configured as shown in FIG. 10. In the stent 1C of FIG. 10, the gap S1 between the second opening section 18 and the umbrella section 50 is configured to be blocked by the umbrella section 50 without communication with the outside of the main body 10 in the circumferential direction of the main body 10. As the stent 1C is configured as described above, the umbrella section 50 can be configured in a compact size.

Figure 11:
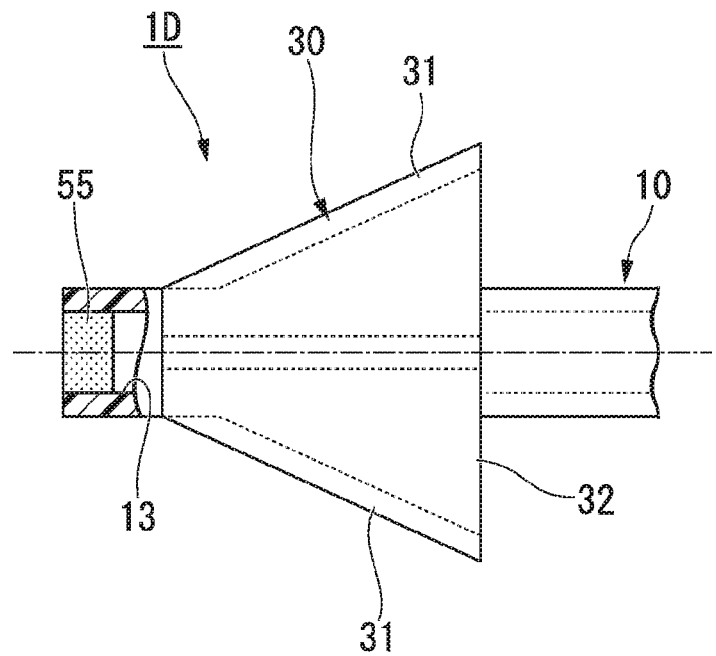
FIG. 11 is a side view of the base end portion of the stent according to the variation of the first embodiment of the present invention, a portion of which is cutaway.

Like a stent 1D shown in FIG. 11, instead of the valve unit 22 of the stent 1 according to the embodiment, a sealing member 55 formed of a material having elasticity such as sponge or the like may be provided. The slit 22a like the above-mentioned valve unit 22 is not previously formed at the sealing member 55. The sealing member 55 partitions the internal space 13 and the outside of the main body 10.

Figure 12:
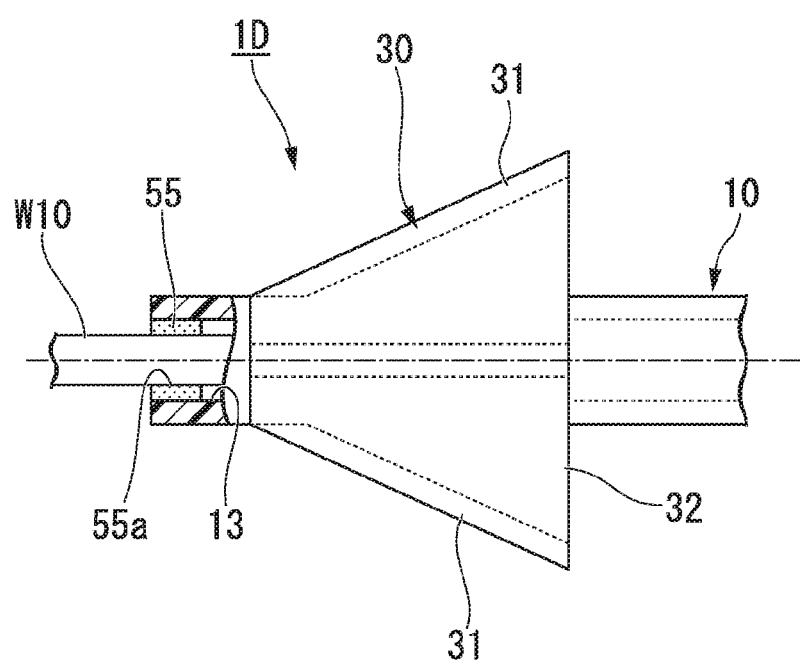
FIG. 12 is a side view of the base end portion showing a state in which a guide catheter is inserted through a sealing member of the stent of FIG. 11, a portion of which is cutaway.

In the implantation method of the stent 1D having the above-mentioned configuration, after the stent 1 having a desired length is selected, the base end side of the guide catheter W10 can be inserted through the internal space 13. As shown in FIG. 12, a through-hole 55a is formed in the sealing member 55 by a method of pushing the guide catheter W10 against the sealing member 55 to break the sealing member 55 or the like. The guide catheter W10 is inserted through the formed through-hole 55a.

When the guide catheter W10 is drawn after the umbrella section 30 is hooked by the duodenal papilla P2, the through-hole 55a is sealed by the elastic force of the sealing member 55.

Even by the stent 1D having the above-mentioned configuration, the same effect as the stent 1 of the embodiment can be exhibited.

Second Embodiment

Next, while a second embodiment of the present invention will be described with reference to FIG. 13, the same components as the first embodiment are designated by the same reference numerals, detailed description thereof will be omitted, and only different points will be described.

Figure 13:
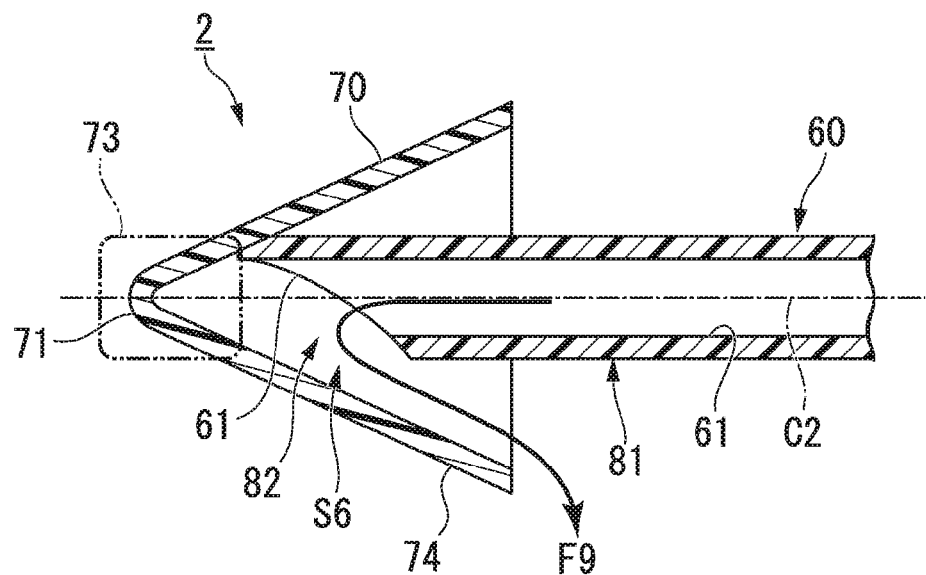
FIG. 13 is a side cross-sectional view of a base end portion of a stent according to a second embodiment of the present invention.

As shown in FIG. 13, a stent 2 according to the embodiment includes a main body 60 formed in a tubular shape, and an umbrella section 70. A notch section 61 is formed at a base end of the main body 60. The umbrella section 70 is formed at the base end of the main body 60.

The main body 60 has the notch section 61 cutout to be inclined from the base end surface of the main body 60 throughout a side surface of a front end side, instead of the second opening sections 18 and 19 of the main body 10 of the first embodiment. An opening by the notch section 61 is opened in an inclined direction at the base end side of the stent 2. The main body 60 may be formed of the same material as the main body 10.

The umbrella section 70 is formed of the same material as the umbrella section 50 of the stent 1C shown in FIG. 10 in a side surface shape of a cone with the same thickness. The umbrella section 70 has a bottom section 70b formed by closing a base end portion (an umbrella base end portion) 72, and is formed to be spaced apart from the outer circumferential surface of the main body 60 outward in the radial direction while extending toward the front end throughout the entire circumference of the main body 60. That is, the umbrella section 70 is formed in a substantially conical shape having a diameter increasing from the base end to the front end of the main body 60.

An outer surface 71 of the base end portion 72 of the umbrella section 70 is formed in a rounded shape. The umbrella section 70 may be formed of a metal mesh as long as the mesh is fine such that food residue cannot pass therethrough.

The base end portion of the main body 60 and the inner surface of the umbrella section 70 are fixed to each other by an adhesive agent or the like in a state in which a longitudinal axis (a central axis) C2 of the main body 60 and a longitudinal axis of the umbrella section 70 coincide with each other.

In the embodiment, when seen in a direction of a longitudinal axis C2 of the umbrella section 70, the main body 60 and a region 73 that is a portion overlapping the main body 60 correspond to a major axis member 81, a region of the umbrella section 70 except for the region 73 corresponds to an inflow prevention section 74. That is, the umbrella section 70 is constituted by the region 73 serving as the base end portion of the major axis member 81 and the inflow prevention section 74.

That is, the base end surface of the major axis member 81 is a bottom section of the region 73 of the umbrella section 70. Accordingly, an opening is not formed in the base end surface of the major axis member 81 serving as the region 73 of the umbrella section 70. A second opening section 82 formed in a side surface of a base end portion of the major axis member 81 and in communication with an internal space 62 of the main body 60 is constituted by the notch section 61 and the region 73 of the umbrella section 70.

In the stent 2 having the above-mentioned configuration, as shown by an arrow F9, bile discharged to the outside of the main body 60 from the second opening section 82 collides with the umbrella section 70 spaced apart by a gap S6 from the second opening section 82 outward in the radial direction of the main body 60 to flow toward the front end.

As described above, according to the stent 2 of the embodiment, it is possible to prevent that the food residue is introduced from the second opening section 82 and flows backward to the bile duct P3 through the internal space 62 of the main body 60.

According to the stent 2 of the embodiment, since the umbrella section 70 is constituted by integrally forming the region 73 and the inflow prevention section 74, the base end portion of the major axis member 81 can be securely closed.

Third Embodiment

Next, a third embodiment of the present invention will be described with reference to FIG. 14, the same components as the first embodiment are designated by the same reference numerals, detailed description thereof will be omitted, and only different points will be described.

Figure 14:
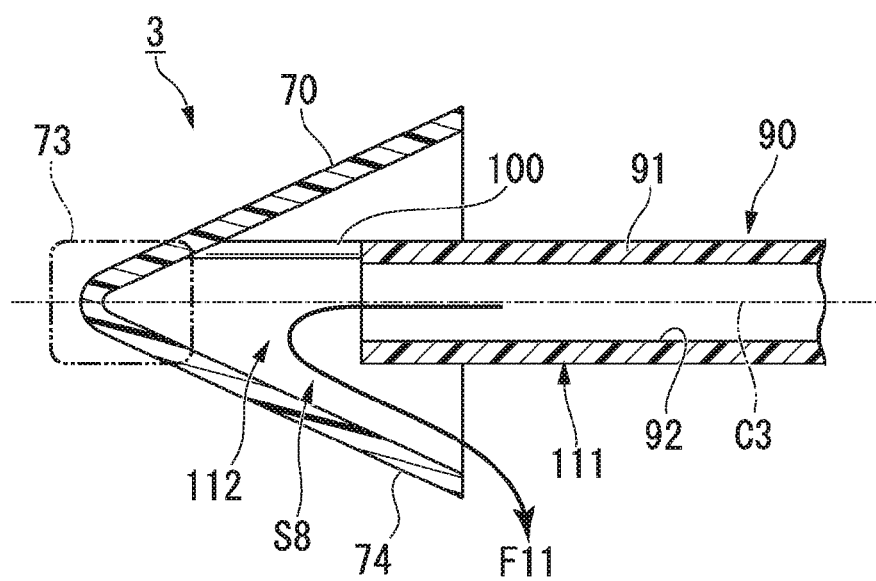
FIG. 14 is a side cross-sectional view of a base end portion of a stent according to a third embodiment of the present invention.

As shown in FIG. 14, a stent 3 according to the embodiment includes a main body 90 formed in a tubular shape, the above-mentioned umbrella section 70, and a joint member 100. The joint member 100 connects the main body 90 and the umbrella section 70 and is formed between the main body 90 and the umbrella section 70.

The main body 90 may be formed of the same material as the main body 10 of the above-mentioned first embodiment or second embodiment.

The joint member 100 is formed in a rod shape extending in a direction along a longitudinal axis (a central axis) C3 of the main body 90. The joint member 100 is formed of stainless steel or a rigid resin material.

The joint member 100 is adhered to the main body 90 to extend from a wall section 91 of the main body 90 toward a base end. The main body 90 and the joint member 100, and the joint member 100 and the umbrella section 70 may be adhered by a known adhesive agent or the like.

A major axis member 111 is constituted by the main body 90, the joint member 100, and the region 73 of the umbrella section 70. The main body 90 corresponds to a front end portion of the major axis member 111, and the region 73 corresponds to a base end portion of the major axis member 111.

A second opening section 112 is disposed between the main body 90 and the region 73 of the umbrella section 70, and formed at a portion except for the joint member 100.

In the stent 3 having the above-mentioned configuration, as shown by an arrow F11, the bile flowed to the outside of the main body 90 from the second opening section 112 collides with the umbrella section 70 spaced by a gap S8 from the second opening section 112 outward in the radial direction of the main body 90, and then, flows toward the front end.

As described above, according to the stent 3 of the embodiment, it is possible to prevent that the food residue is introduced from the second opening section 112 and a backward flow to the bile duct P3 through an internal space 92 of the main body 90.

Hereinabove, while the first to third embodiments of the present invention have been described with reference to the accompanying drawings, the specific configuration is not limited to the embodiments but may include various configurations without departing from the spirit of the present invention. Further, the configurations shown in the embodiments can be appropriately combined and used.

For example, in the first to third embodiments, the configuration in which the main body is formed in a tubular shape has been shown. However, a cross-sectional shape by a surface perpendicular to the longitudinal axis of the main body may be formed in a contour having an oval shape or a polygonal shape such as a hexagonal shape or the like, in addition to a circular shape.

In the first to third embodiments, the configuration in which the main body is formed of a resin material of one layer has been shown. However, the main body may be constituted by a plurality of layers disposed to be concentric with the main body. When the main body is constituted by two layers, an outer layer disposed at the outer circumferential surface side of the main body formed in the tubular shape may be formed of a resin material having elasticity, flexibility and biocompatibility such as urethane, polyethylene, or the like. Then, an inner layer disposed at the inner circumferential surface side of the main body formed in the tubular shape may be formed of a resin material such as PTFE, PFA, or the like.

In the first embodiment, the configuration in which the four bony portions 31 that constitute the umbrella section 30 are disposed at intervals of equal angle around the longitudinal axis C1 has been shown. However, the bony portions 31 may not be disposed at intervals of equal angle around the longitudinal axis C1.

In the first embodiment, the configuration in which the number of bony portions 31 that constitute the umbrella section 30 is four has been shown. However, the number of bony portions 31 that constitute the umbrella section 30 is not limited thereto but may be 1 to 3 and 5 or more.

In the first embodiment, the configuration in which the membranous portions 32 are formed between all of the neighboring bony portions 31 has been shown. However, the inflow prevention surface may be formed to cover the second opening section within a range in which the food residue or the like can be prevented from being introduced into the stent via the second opening section in a state in which the stent is implanted in the target area. For example, the membranous portion may be formed between a set of neighboring bony portions, and in the circumferential direction of the main body, the inflow prevention surface configured to cover the second opening section throughout a half circumference may be formed.

In the first embodiment, the configuration in which the four flaps 40 are fixed to the front end portion 11 of the main body 10 has been shown. However, the flaps 40 may not be provided at the stent.

In the first to third embodiments, lumen tissue into which the stent is implanted was the bile duct P3. However, the lumen tissue is not limited to the bile duct P3 but may be, for example, a pancreatic duct or the like.

Hereinabove, while the embodiments of the present invention have been described, the technical spirit of the present invention is not limited to the embodiments but may change combinations of the components in the embodiments, add various modifications to the components or delete the components without departing from the spirit of the present invention. The present invention is not limited to the above-mentioned description and is only limited by the scope of the following claims.

A stent capable of suppressing introduction of a fluid such as a food residue or the like from the second opening section and a backward flow through the internal space of the main body can be provided.

What is claimed is:

1. A stent comprising:
a major axis member that includes:
an outer circumferential surface having a tubular shape and an internal space that extends from a front end portion to a base end portion of the outer circumferential surface,
a first opening section provided at the front end portion of the outer circumferential surface, the first opening section being in communication with the internal space, and
a second opening section disposed on the outer circumferential surface, the second opening section being in communication with the internal space; and
an inflow prevention section that has an inflow prevention surface covering the entire second opening section,
the inflow prevention section having a first edge section that is fixed nearer to the base end portion side than the second opening section, and a second edge section that is disposed at a position radially spaced from the outer circumferential surface and radially spaced from the second opening section such that the second edge section extends outward in a radial direction from the second opening section.

2. The stent according to claim 1, the inflow prevention section further including:
a plurality of bony portions that is arranged in a circumferential direction of the major axis member,
each bony portion having a first end section formed of a material having elasticity and fixed closer to the base end portion than the second opening section, and a second end section extending toward the front end portion in a natural state and radially spaced apart from the outer circumferential surface such that the second end section extends outward in the radial direction; and
membranous portions that have more flexibly than the bony portions and that are formed between the bony portions such that the membranous portions are disposed between at least one set of neighboring bony portions in the circumferential direction from the first end section to the second end section,
wherein the inflow prevention surface covers the second opening section.

3. The stent according to claim 2, wherein:
the membranous portions are provided between the neighboring bony portions in the circumferential direction of the major axis member around an entire circumference of the major axis member, and
a cutout, which extends from the front end portion to the base end portion and which penetrates through the membranous portion in a thickness direction, is formed in one of the membranous portions.

4. The stent according to claim 1, wherein the inflow prevention section is disposed around an entire circumference of the major axis member.

5. The stent according to claim 1, wherein:
the inflow prevention surface extends from a base end, disposed at the base end portion, towards the front end portion,
the inflow prevention surface extends from the outer circumferential surface of the major axis member such that a portion of the inflow prevention surface is spaced radially outward around an entire circumference of the major axis member, and
the second opening section is provided between a bottom section of the inflow prevention surface and the base end portion of the major axis member, and
the second opening section forms a crevice that is covered by the inflow prevention surface.

6. The stent according to claim 5, further comprising a joint member that is disposed between the distal end of the outer circumferential surface and the base end of the inflow prevention surface,
the joint member extending from a wall section of the base end portion toward the base end,
the joint member being formed in a rod shape,
the joint member connecting the distal end of the outer circumferential surface and the base end, and
the second opening section being formed by the joint member and the major axis member.

7. The stent according to claim 1, wherein a valve unit, which is formed of a material having elasticity and which has a slit that is closed in a natural state and that elastically deforms to communicate with the internal space, is disposed at the base end portion.

8. The stent according to claim 1, wherein a sealing member, which is formed of a material having elasticity and which partitions the internal space and the outside of the major axis member, is disposed at the base end portion.

9. The stent according to claim 1, wherein the second opening section is proximal of a distal end of the outer circumferential surface.

* * * * *